US010808281B2

(12) United States Patent
Glökler et al.

(10) Patent No.: US 10,808,281 B2
(45) Date of Patent: *Oct. 20, 2020

(54) ELECTROCHEMICAL DETECTION OF POLYMERASE REACTIONS BY SPECIFIC METAL-PHOSPHATE COMPLEX FORMATION

(71) Applicants: Jörn Glökler, Berlin (DE); Amaryllis Innovation GmbH, Berlin (DE)

(72) Inventors: Jörn Glökler, Berlin (DE); Fred Lisdat, Waldau (DE)

(73) Assignees: Jörn Glökler, Berlin (DE); AMARYLLIS INNOVATION GMBH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/058,579

(22) Filed: Aug. 8, 2018

(65) Prior Publication Data

US 2019/0062826 A1 Feb. 28, 2019

Related U.S. Application Data

(62) Division of application No. 14/399,491, filed as application No. PCT/EP2013/059615 on May 8, 2013, now abandoned.

(30) Foreign Application Priority Data

May 11, 2012 (EP) .................................. 12167723

(51) Int. Cl.
*C12Q 1/6869* (2018.01)
*G01N 33/84* (2006.01)

(52) U.S. Cl.
CPC .......... *C12Q 1/6869* (2013.01); *G01N 33/84* (2013.01)

(58) Field of Classification Search
CPC .......................... G01N 33/84; C12Q 1/6869; C12Q 2531/113; C12Q 2563/137; C12Q 2563/301
See application file for complete search history.

(56) References Cited

U.S. PATENT DOCUMENTS

| 4,458,006 | A | 7/1984 | Donges et al. |
| 6,210,891 | B1 | 4/2001 | Nyren et al. |
| 6,258,568 | B1 | 7/2001 | Nyren |
| 6,613,205 | B1* | 9/2003 | Steiner ............... G01N 27/3272 204/403.01 |

(Continued)

FOREIGN PATENT DOCUMENTS

| EP | 13724767.2 | 5/2013 |
| EP | 2847595 | 3/2015 |

(Continued)

OTHER PUBLICATIONS

Hayes et al, Manganese Substantially Alters the Dynamics of Translesion DNA Synthesis, 2002, Biochemistry 41, 4771-4778.*

(Continued)

*Primary Examiner* — Bethany L Martin
(74) *Attorney, Agent, or Firm* — Ballard Spahr LLP

(57) ABSTRACT

The present invention relates to a nucleic acid sequencing method that determines the sequence of a template nucleic acid by electrochemical means via the depletion of metal ions as a result of its binding to and/or precipitation with pyrophosphate.

5 Claims, 2 Drawing Sheets

(56) References Cited

U.S. PATENT DOCUMENTS

Figure 1:
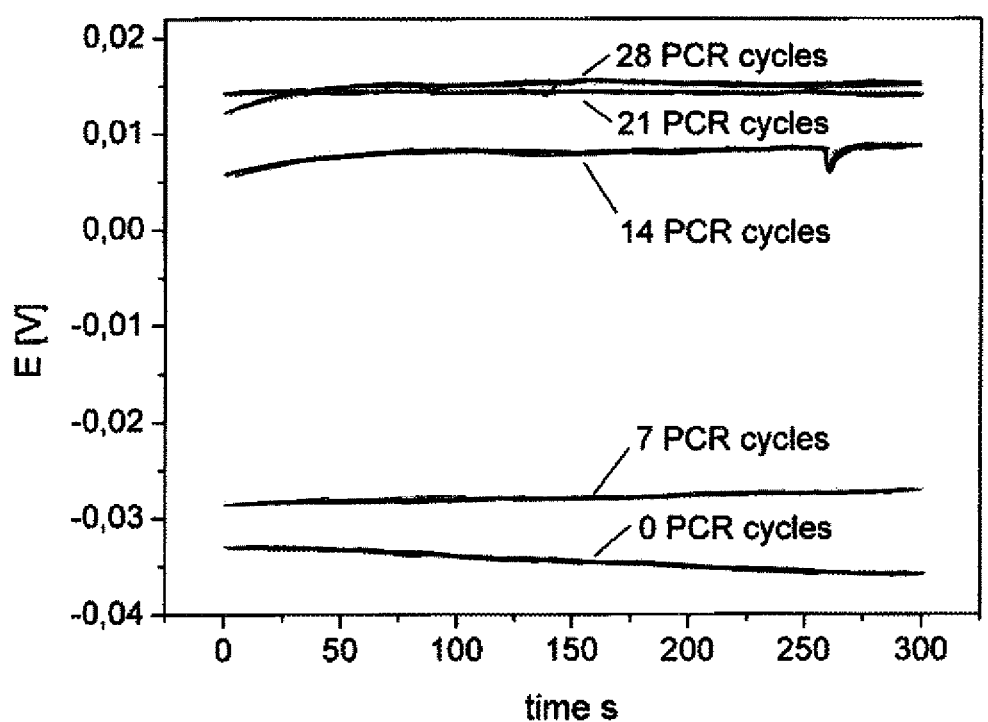

| | | | |
|---|---|---|---|
| 2002/0055100 | A1 | 5/2002 | Kawashima et al. |
| 2003/0108896 | A1 | 6/2003 | Vogt |
| 2006/0029948 | A1 | 2/2006 | Lim et al. |
| 2011/0159481 | A1* | 6/2011 | Liu .................. C12Q 1/48 |
| | | | 435/6.11 |

FOREIGN PATENT DOCUMENTS

| | | |
|---|---|---|
| JP | 2007037483 | 2/2007 |
| WO | WO 2007/048033 | 4/2007 |
| WO | WO 2010/047804 | 4/2010 |
| WO | PCT/EP2013/059615 | 5/2013 |
| WO | WO 2013/167668 | 11/2013 |

OTHER PUBLICATIONS

U.S. Appl. No. 14/940,731, filed Nov. 13, 2015, Jörn Glökler.
Ex Parte Quayle was issued on Sep. 27, 2019 by the USPTO for U.S. Appl. No. 16/058,646, filed Aug. 8, 2018 and published as US 2018-0346978 A1 on Dec. 6, 2018 (Inventor—Jörn Glökler) (5 Pages).
Abbaspour et al., "A selective and sensitive carbon composite coated platinum electrode for aluminium determination in pharmaceutical and mineral water samples", Anal. Chim.Acta., vol. 662, No. 1, pp. 76-81.
Ahmadian et al., "Pyrosequencing: history, biochemistry and future", Clin Chim Acta. (2006), vol. 363, No. 1-2, pp. 83-94.
Beaucage et al., "Deoxynucleoside phosphoramidites—A new class of key intermediates for deoxypolynucleotide synthesis", Tetrahedron Letters, (1981), vol. 22, pp. 1859-1862.
Chelation, New World Encyclopedia, 2008.
Cigala et al., "Quantitative study on the interaction of $Sn^{2+}$ and $Zn^{2+}$ with some phosphate ligands, in aqueous solution at different ionic strengths", Journal of Molecular Liquids, vol. 165, pp. 143-153.
Credo et al., "Label-free electrical detection of pyrophosphate generated from DNA polymerase reactions on field-effect devices", Analyst, vol. 137, pp. 1351-1361.
Franca et al., "A review of DNA sequencing techniques", Quarterly Reviews of Biophysics, (2002), vol. 35, No. 2, pp. 169-200.
Herdewijn, "Redesigning the leaving group in nucleic acid polymerization", FEBS LETT., vol. 586, No. 15, pp. 2049-2056.
Harris et al., "A comparative study of aluminum(III), gallium(III), indium(III), and thallium(III) binding to human serum transferrin", Coordination Chemistry Reviews, (2002), vol. 228, No. 2, pp. 237-262.
Lohani et al., "Colorimetric and fluorescent sensing of pyrophosphate in 100% aqueous solution by a system comprised of rhodamine B compound and $Al^{3+}$ complex", Analyst, (2010), 135, 2079-2084.
Midgley D., et al., "The manganese(IV) oxide electrode as a manganese(II) sensor", Talanta, vol. 32, No. 1, pp. 7-10.
Rothberg et al., "An integrated semiconductor device enabling non-optical genome sequencing", Nature, vol. 475, No. 7356, pp. 348-352.
Sabbioni et al., "Effects of trace metal compounds on HIV-1 reverse transcriptase", Biol. Trace Element Res.,(1999),vol. 68, pp. 107-119.
Song, Q., et al., "Pyrosequencing on Nicked dsDNA Generated by Nicking Endonucleases", Analytical Chemistry, vol. 82, No. 5, pp. 2074-2081.
Spangler et al., "Luminescent lanthanide complexes as probes for the determination of enzyme activities", Ann. N. Y. Acad. Sci., (2008), vol. 1130, pp. 138-148.
Tomita et al., "Loop-mediated isothermal amplification (LAMP) of gene sequences and simple visual detection of products". Nat Protoc. 2008; 3:877-82.
Wu et al., "3'-O-modified nucleotides as reversible terminators for pyrosequencing", PNAS, (2007), vol. 104, No. 42, pp. 16462-16467.
International Search Report and Written Opinion dated Jun. 19, 2013 by the International Searching Authority for International Application No. PCT/EP2013/059615, filed on May 8, 2013 and published as WO 2013/167668 on Nov. 14, 2013 (Applicant—Alacris Theranostics GMBH) (8 Pages).
International Preliminary Report on Patentability dated Nov. 11, 2014 by the International Searching Authority for International Application No. PCT/EP2013/059615, filed on May 8, 2013 and published as WO 2013/167668 on Nov. 14, 2013 (Applicant—Alacris Theranostics GMBH) (5 Pages).
Preliminary Amendment dated Apr. 29, 2015 to the USPTO for U.S. Appl. No. 14/399,491, filed May 8, 2013 and published as US 2015/0159208 A1 on Jun. 11, 2015 (Inventor—Jörn Glökler) (5 Pages).
Requirement for Restriction/ Election dated Mar. 31, 2017 by the USPTO for U.S. Appl. No. 14/399,491, filed May 8, 2013 and published as US 2015/0159208 A1 on Jun. 11, 2015 (Inventor—Jörn Glökler) (9 Pages).
Response to Requirement for Restriction/ Election dated May 31, 2017 to the USPTO for U.S. Appl. No. 14/399,491, filed May 8, 2013 and published as US 2015/0159208 A1 on Jun. 11, 2015 (Inventor—Jörn Glökler) (5 Pages).
Non Final Rejection dated Jul. 5, 2017 by the USPTO for U.S. Appl. No. 14/399,491, filed May 8, 2013 and published as US 2015/0159208 A1 on Jun. 11, 2015 (Inventor—Jörn Glökler) (10 Pages).
Response to Non Final Rejection dated Oct. 30, 2017 to the USPTO for U.S. Appl. No. 14/399,491, filed May 8, 2013 and published as US 2015/0159208 A1 on Jun. 11, 2015 (Inventor—Jörn Glökler) (8 Pages).
Final Rejection dated Nov. 16, 2017 by the USPTO for U.S. Appl. No. 14/399,491, filed May 8, 2013 and published as US 2015/0159208 A1 on Jun. 11, 2015 (Inventor—Jörn Glökler) (8 Pages).
Response to Final Rejection and Request for Continued Examination (RCE) dated Feb. 20, 2018 to the USPTO for U.S. Appl. No. 14/399,491, filed May 8, 2013 and published as US 2015/0159208 A1 on Jun. 11, 2015 (Inventor—Jörn Glökler) (10 Pages).
Final Rejection dated Apr. 20, 2018 by the USPTO for U.S. Appl. No. 14/399,491, filed May 8, 2013 and published as US 2015/0159208 A1 on Jun. 11, 2015 (Inventor—Jörn Glökler) (9 Pages).
Communication pursuant to Article 94(3) EPC dated Oct. 10, 2016 for application EP 13724767.2, filed on May 8, 2013 and published as EP 2847595 on Mar. 18, 2015 (Applicant—Alacris Theranostics GmbH) (8 pages).
Decision to Grant a European Patent pursuant to Article 97(1) EPC was mailed Feb. 1, 2018 for application EP13724767.2, filed on May 8, 2013 and published as EP 2847595 on Mar. 18, 2015 (Applicant—Alacris Theranostics GmbH) (2 pages).

* cited by examiner

ELECTROCHEMICAL DETECTION OF POLYMERASE REACTIONS BY SPECIFIC METAL-PHOSPHATE COMPLEX FORMATION

CROSS REFERENCE TO RELATED APPLICATIONS

This application is a continuing application of U.S. application Ser. No. 14/399,491, filed Nov. 6, 2014, which is a national phase application of PCT/EP2013/059615, filed May 8, 2013, which claims priority to European Application No. 12167723.1, filed May 11, 2012, the disclosure of each is herein incorporated by reference in its entirety.

FIELD OF THE INVENTION

The present invention is in the field of chemistry and biology. Specifically, the invention relates to the electrochemical detection of pyrophosphate and to electrochemical nucleic acid sequencing.

INTRODUCTION

Nucleic acid polymerase reactions are central to a multitude of sensitive detection methods. Especially many different solutions have been developed for PCR product formation. More specifically, a certain reaction used to identify a DNA sequence termed pyrosequencing (Ahmadian et al. Clin. Chim. Acta. 2006. 363(1-483-94) is of great interest. In pyrosequencing the four different nucleotides are added to a polymerase reaction in alternating cycles and the release of pyrophosphate is monitored indirectly.

Currently, two main approaches for the detection of product formation from a polymerase reaction such as a nucleic acid sequencing method exist:

Pyrophosphate is used to generate ATP via sulfurylase and ADPS, which leads to light emission by luciferase (Ahmadian et al. Clin. Chico. Acta. 2006. 363(1-2):83-94). The light is detected and corresponds to a given reaction by polymerase. As a disadvantage, this method utilizes expensive and unstable agents, such as enzymes and ATP.

Another method is employed by Ion Torrent that measures the polymerase reaction by a change in pH (Rothberg et al. Nature. 2011 Jul. 21; 475(7354348-52). The reaction liberates one extra 11+-ion which is detected by a chemFET or ISFET (see WO2010047804). The advantage of this method is a simple adaptation for integrated circuits which allows considerable miniaturization and parallelization. No extra enzymes other than the polymerase are necessary. However, the reaction needs to occur largely unbuffered and suffers from a low sensitivity.

In other methods pyrophosphate is detected by complexation with certain metal ions. Calcein/$Mn^{2}$+ is a colorless complex, which becomes fluorescent when the manganese is depleted and occupied with magnesium (Tomita et al. Nat Protoc. 2008; 3(5):877-82.). Alternatively, pyrophosphate has been used to measure manganese ions in solution by optical means (Takashima et al. J. American Chem. Soc. [Internet]. 2011 Dec. 28).

Aluminum ions also form a tight specific complex with pyrophosphate. A fluorescent rhodarnine/$Al^{3+}$ complex is depleted of aluminum by the synthesis of pyrophosphate and thus becomes colorless for detection (Lohani et al. Analyst. 2010. 135(8):2079-84). Free, uncomplexed AI(I11) can be detected with ISFET (Abbaspour et al. Anal. Chim. Acta. 2010 Mar. 3; 662(1):76-81.). A chelator-modified silicon-on-insulator field-effect transistor (SOI-FET) with bound $Zn^2$ ions has been shown to detect pyrophosphate liberated by a polymerase reaction directly (Credo et al. The Analyst [Internet]. 2012 Jan. 19). Several other metal ions are known to be specifically displaced from complexes (e.g. transferrin) by pyrophosphate, e.g. $Fe^{3+}$, $Ga^3$+, $In^3$+ (Harris et al. Coordination Chemistry Reviews. 2002. 228(2):237-62), Sn'. and $Zn^2$ (Cigala et al. Journal of Molecular Liquids, 2012. 165:143-153), Some lanthanide metal ions such as terbium, europium and ytterbium are known to bind to phosphate species such as triphosphates, DNA, pyrophosphate, and phosphate, albeit with different affinities (Spangler et al. Ann. N. V. Acad. Sci. 2008. 1130:138-48.). These metal ions can be used either free or in complex with certain ligands that may increase their specificity. So far, these measurements were conducted by using the unique fluorescence properties of lanthanides.

The main approaches suffer from the drawback that they either require expensive and unstable agents, or the reaction is carried out in a largely unbuffered system and has a low sensitivity. Methods based on the formation of metal ion/pyrophosphate complexes require extra hardware such as optical devices or special surface receptors (for the method of Credo et al.) which is expensive and hard to implement into existing sequencing units.

The problem to be solved by the present invention may be formulated as the provision of an inexpensive and simple method for a fast and sensitive detection of nucleic acid polymerase activity with a potential for miniaturization and parallelization. Ideally, the method may be integrated into current systems such as sequencing devices without or with few modifications.

Definitions

Sample

A sample refers to any kind of chemical or biological substance or substance mixture comprising a nucleic acid, wherein the sequence or part of the sequence of the nucleic acid is of interest. A sample may stem from or comprise a prokaryote or an eukaryote, such as an archaeon, a bacterium, a protist, a fungus, a virus, a viroid, a plant or an animal.

Nucleic Acid

The term (template) nucleic acid is here used in its broadest sense and comprises ribonucleic acids (RNA) and deoxyribonucleic acids (DNA) from all possible sources, in all lengths and configurations, such as double-stranded, single-stranded, circular, linear or branched. AU sub-units and sub-types are also comprised, such as monomeric nucleotides, oligomers, plasmids, viral and bacterial nucleic acids, as well as genomic and non-genomic DNA and RNA from animal and plant cells or other eukaryotes or prokaryotes, mRNA (messenger RNA) in processed and unprocessed form, tRNA (transfer RNA), hn-RNA (heterogeneous nuclear RNA), rRNA (ribosomal RNA), LNA (locked nucleic acid), mtRNA (mitochondrial), nRNA (nuclear RNA), siRNA (short interfering RNA), snRNA (small nuclear RNA), snoRNA (small nucleolar RNA), scaRNA (Small Cajal Body specific RNA), microRNA, dsRNA (double-stranded RNA), ribozyme, riboswitch, viral RNA, dsDNA (double-stranded DNA), ssDNA (single-stranded DNA), plasmid DNA, cosmid DNA, chromosomal DNA, viral DNA, mtDNA (mitochondrial DNA), nDNA (nuclear DNA), snDNA (small nuclear DNA) or the like or as well as all other conceivable nucleic acids.

Sometimes the concentration of the nucleic acid to be sequenced (template nucleic acid) may be too low for sequencing. In this case, the sample may be subjected to an amplification method prior to sequencing. Nucleic-acid amplification can be accomplished by any of the various nucleic-acid amplification methods known in the art, including but not limited to the polymerase chain reaction (PCR), ligase chain reaction (LCR), transcription-based amplification system (TAS), nucleic acid sequence based amplification (NASBA), rolling circle amplification (RCA), transcription-mediated amplification (TMA), self-sustaining sequence replication (3SR) and Q3 amplification. In a preferred embodiment the amplification method is selected from the group of polymerase chain reaction (PCR), real-time PCR (rtPCR), helicase-dependent amplification (HDA) and recombinase-polymerase amplification (RPA).

Primer

The sequence of the primer (molecule) may be a random sequence. However, in cases where part of the sequence of the template nucleic acid is already known the primer can be designed to be complementary to such a sequence. In one embodiment, the primer anneals to either the 3' or the 5' end of the template nucleic acid. The primer may be prepared using any suitable method, such as, for example, the phosphotriester and phosphodiester methods or automated embodiments thereof. In one such automated embodiment diethylophosphoramidites are used as starting materials and may be synthesized as described by Beaucage et al. Tetrahedron Letters. 1981. 22:1859-1862. One method for synthesizing oligonucleotides on a modified solid support is described in U.S. Pat. No. 4,458,006, which is hereby incorporated by reference. It is also possible to use a primer which has been isolated from a biological source (such as a restriction endonuclease digest).

Preferred primers have a length of about 15-100, more preferably about 20-50, most preferably about 20-40 bases.

Nucleotides

As used herein, the term nucleotides refer to deoxyribonucleoside polyphosphates, such as deoxyribonucleoside triphosphates (dNTPs). Non-limiting examples of such dNTPs are dATP, dGTP, dCTP, dTTP, dUTP, which may also be present in the form of labelled derivatives, for instance comprising a fluorescent label, a radioactive label, a biotin label. dNTPs with modified nucleotide bases are also encompassed, wherein the nucleotide bases are for example hypoxanthine, xanthine, 7-methylguanine, inosine, xanthinosine, 7-methylguanosine, 5,6-dihydrouracil, 5-methyl cytosine, pseudouridine, dihydrouridine, 5-methyl cytidine. Deoxyribonucleoside polyphosphates, i.e. nucleotides with more than 3 phosphates, are also utilized by polymerases. In this case the polymerase reaction does not generate pyrophosphate. However, the principle of selecting a metal ion for binding to other phosphates (such as triphosphate) and using it for electrochemical detecting said phosphate can be applied correspondingly.

Elongation

Nucleic acid elongation herein means the stepwise addition of nucleotides to the growing nucleic acid chain. Elongation is catalyzed by a polymerase. Herein, a polymerase include but are not limited to T7 DNA polymerase, DNA Polymerase γ, *Escherichia coli* DNA pol I, *Thermus aquaticus* pol I, *Bacillus stearothermophilus* pol I, Pol II (bacterial), Phi29 DNA polymerase, Pol B (archaebacterial), Pol α, δ, ε and ζ eukaryotic polymerase pol β, pol σ, pol λ, pol μ, terminal deoxynucleotidyltransferase (TdT), Poi X polymerase and Pol IV.

Sequencing

Nucleic acid sequencing can consist of determining whether a particular nucleic acid differs in sequence from a reference nucleic acid, confirming the presence of a particular nucleic acid sequence in a sample, determining partial sequence information such as the identity of one or more nucleotides within a nucleic acid, determining the identity and order of nucleotides within a nucleic acid, etc.

Most sequencing methods relate to the sequencing of DNA. Current methods, thus, typically require RNA to be converted to complementary DNA (cDNA) via reverse transcription prior to sequencing. Thus, if RNA is to be sequenced, the RNA may be first reverse transcribed into cDNA.

Annealing

Annealing refers to the pairing of the primer by hydrogen bonds to a complementary sequence on the template nucleic acid, forming a double-stranded polynucleotide. Annealing may be facilitated by decreasing the temperature.

Electrode Measurements

Electrochemical measurements may be made in an electrochemical cell consisting of two or more electrodes and the electronic circuitry for controlling and measuring the current and the potential.

The simplest electrochemical cell uses two electrodes. The potential of one electrode is sensitive to the analyte's concentration, and is called the working electrode or the indicator electrode, herein only electrode. The second electrode, which is called reference electrode, completes the electrical circuit and provides a reference potential against which the working electrode's potential is measured. Ideally the reference electrode's potential remains constant so that one can assign to the working electrode any change in the overall cell potential.

Potentiometry is the field of electroanalytical chemistry in which potential is measured under the conditions of no current flow. The measured potential may then be used to determine the analytical quantity of interest, generally the concentration of some component of the analyte solution. The potential that develops in the electrochemical cell is the result of the free energy change that would occur if the chemical phenomena were to proceed until the equilibrium condition has been satisfied.

A reference electrode is an electrode which has a stable and well-known electrode potential. Reference electrodes are well-known to the skilled person.

DETAILED DESCRIPTION OF THE INVENTION

The inventors have unexpectedly found that biological reactions which release pyrophosphate may be detected by electrochemical methods via the formation of pyrophosphate/metal ion complexes and/or precipitates.

The present invention is based on the principle that pyrophosphate (PPi; inorganic diphosphate) can be bound and/or precipitated directly in a biological reaction (in a reaction mixture). The binding and/or precipitation decreases the concentration of unbound and/or dissolved (free) PPi which changes the concentration of a metal ion, subsequently resulting in a change of signal generation in an electrochemical sensor.

A typical PPi releasing reaction is a reaction that uses the synthetic activity of a polymerase. For example, DNA polymerase catalyses the polymerization of deoxyribanucleotides (dNTPs) into a DNA strand. The addition of one of the four complementary dNTPs onto the template releases PPi stoichiometrically. This principle can be exploited in that the synthetic activity of the polymerase is determined indirectly over the release of PPi. In contrast to the present methods, the depletion of metal ions as a result of the binding to and/or the precipitation with PPi is detected by electrochemical means. Metal ions that bind to the pyrophosphate anion specifically in the presence of triphosphates and nucleic acids can thereby be used as an indicator for polymerase reactions. Free metal ions can be detected by electrochemical methods and thus indirectly indicate the amount of pyrophosphate complex formed by the reaction despite the presence of triphosphates and oligonucleotides. The decrease in free metal ion concentration results in a corresponding signal drop at an electrode. This will occur only if a nucleotide matching to the template is offered to the polymerase. Thus, this technique can be applied to the detection of nucleic acid sequencing reactions.

Sequencing

Accordingly, in a first aspect the present invention relates to an electrochemical nucleic acid sequencing method comprising the steps of (a) providing a sample comprising a template nucleic acid to be sequenced; (b) annealing a primer molecule to said template nucleic acid; (c) carrying out nucleic acid elongation steps with a polymerase on said template in the presence of metal ions, wherein each step comprises the addition of a single type of nucleotide, wherein pyrophosphate is released in a stoichiometric ratio to the number of nucleotides incorporated, and wherein the metal ions are capable of specifically binding to pyrophosphate; (d) determining in said sample the change of potential, current or charge at an electrode and (e) correlating this change in potential, current or charge over the number of elongation steps with the type of nucleotides added.

To correlate the signal observed with the sequence of the template nucleic acid to be sequenced one may proceed as follows:

A change in the signal may be observed, once a nucleotide is successfully incorporated. Since only one type of nucleotide (adenine A, cytosine C, guanine 6, or uracil Uithymine T) is added at the same time, one can deduce the type of incorporated (elongated) nucleotide. Repeating the steps of adding types of nucleotides and observing the signal one may further deduce the whole sequence of the template nucleic acid.

Preferably, a calibration curve is generated by measuring the signal at various known concentrations of metal ions used for binding and/or precipitating pyrophosphate in order to ascertain confidence parameters. For example pyrophosphate may be added in various known concentrations to a solution of constant metal ion concentration in another experiment. The calibration curve is preferably made in a solution (e.g. a buffer) which is comparable to the test solution (e.g. sequencing buffer). in the test solution the initial metal ion concentration may be known or calculated from the initial signal.

Preferably, the nucleic acid sequencing method is based on pyrosequencing, reversible-terminator-pyrosequencing, or closed complex formation sequencing.

It is preferred that step d. and optionally step e. is done after each elongation step c. Alternatively, step d. and optionally step e. is done after every second, third, fourth, firth or even more elongation steps c.

The sequencing method according to the invention is preferably based on pyrosequencing. Pyrosequencing is based on the detection of the pyrophosphate (PPi) that is released during DNA polymerization (see, e.g., U.S. Pat. Nos. 6,210,891 and 6,258,568). While avoiding the need for electrophoretic separation, pyrosequencing suffers from a large number of drawbacks that have as yet limited its widespread applicability (Franca et al. Quarterly Reviews of Biophysics. 2002. 35(2):169-200). In an alternative embodiment the step of sequencing involves reversible-terminator-pyrosequencing. The method is extensively explained in Wu et al. PNAS. 2007. 104(42):16462-16467, which is hereby incorporated by reference.

In yet another embodiment sequencing involves closed complex formation sequencing. The method is described in WO 2007/048033, which is hereby incorporated by reference.

Polymerase Reaction

The inventive concept is particularly advantageous in the case of sequencing a nucleic acid. There are, however, other cases where it is desirably to detect and/or quantify the amount (e.g. concentration) or a change in said amount of PPi with a fast and cost-effective method. Consequently, the invention relates to a method for detecting a nucleic acid polymerase reaction comprising the steps of (a) providing a sample comprising a nucleic acid; (b) carrying out a nucleic acid polymerase reaction step on said sample in the presence of metal ions, wherein pyrophosphate is released or depleted depending on the type of polymerase reaction, and wherein the metal ions are capable of specifically binding to pyrophosphate; (c) determining the potential, current or charge at an electrode at least twice, wherein between the first time and the second time one or more nucleic acid polymerase reaction steps take place; and (d) correlating the difference in potential, current or charge over the number of polymerase reaction steps and/or time with the progress of the nucleic acid polymerase reaction.

It is preferred that the nucleic acid polymerase reaction is a synthesis reaction, an amplification reaction and/or a transcription reaction.

It is further preferred that the step of determining the potential, current or charge (step c.) and optionally the step of correlating the difference in potential, current or charge step (step d.) is done after each polymerase reaction step (step b.). Alternatively, step c. and optionally step d. is done after every second, third, fourth, firth or even more elongation polymerase reaction steps.

As described above, the principle can generally be utilized for assessing whether the concentration of pyrophosphate changes in a sample. The method of detecting the formation or depletion of pyrophosphate in a sample comprises the following steps: (a) providing a sample in which pyrophosphate is formed or depleted; (b) adding to said sample metal ions, wherein the metal ions are capable of specifically binding pyrophosphate; (c) determining the potential, current or charge in the sample a first and at least a second time; (d) correlating the difference in potential, current or charge over time with the formation or depletion of pyrophosphate in the sample.

Further, the invention can further be used for detecting the presence and/or the quantity, e.g. concentration, of pyrophosphate in a sample. This method comprises the steps of (a) adding to a sample comprising pyrophosphate a predetermined amount of metal ions or metal ions of a known potential, current or charge, wherein the metal ions are capable of specifically binding pyrophosphate; (b) determining in said sample the potential, current or charge at an electrode; and (c) correlating the potential, current or charge with the amount of pyrophosphate present in said sample.

Metal Ions

There are a number of different metal ions that can bind to and/or precipitate pyrophosphate and, thus, be used in the present method. Preferred metal ions are manganese ions, tin ions, zinc ions, aluminium ions, iron ions, indium ions, gallium ions, zirconium ions, and lanthanides. More preferred metal ions are manganese ions, aluminium ions, tin ions and iron ions. Most preferred metal ions are manganese ions.

Electrochemical Measurements

The present invention is not restricted to a particular electrochemical technique. For example, potentiometry, controlled-current coulometry, amperometry, controlled-potential coulometry, stripping voltammetry, hydrodynamic voltammetry, polarography and stationary electrode voltammetry, pulse polarography and voltammetry and cyclic voltammetry may be used.

Herein, however, potentiometry is preferred, since it is simple, inexpensive and may be further miniaturized. Furthermore, potentiometry is a quantitative technique. The skilled person will readily understand that and how the principle may be transferred to other electrochemical techniques.

The working electrode must be selected such that it responds to the metal ion used for binding and/or precipitation. This means that e.g. for a potentiometric detection the potential of the electrode depends on the concentration of said metal ion. In certain cases it may be advantageous that the electrode is selective for the metal ion. But this may not be necessary in cases where the composition of the solution can be controlled such as in the case of nucleic acid elongation. Preferred working electrodes are electrodes based on manganese oxide. They show a signal which correlates to the concentration of the potential determining ion, i.e. manganese, in solution.

As reference electrode, which provides a stable potential, for example a silver/silver chloride or a saturated calomel electrode (SCE) may be used in the inventive method. Preferably, the reference electrode is a silver/silver chloride electrode with a salt bridge. But also miniaturized reference electrode constructions are possible.

In a specific embodiment, the metal ions are manganese ions and the electrode is a manganese oxide electrode and the reference electrode is a silver/silver chloride electrode.

The present method has a number of advantages: The method is simple, cost-effective and may be easy implemented into existing devices. Moreover, since buffer conditions and components during pyrosequencing can be highly controlled, even less specifically binding and/or precipitating metal ions can be used to monitor the polymerase reaction.

Identification Procedure for Suitable Combination of Metal Ion/Working Electrode In general, for identifying further working electrodes one may first select suitable metal ions and then chose the corresponding working electrode. The type of metal ion should be selected such that they meet one or more of the following criteria. Ideally, the metal ions selected meet all criteria: (1) The metal ions bind and/or precipitate PPi, preferably specifically. In some cases, metal ions binding to and/or precipitating Phosphate (Pi) may be also used. In this case, a pyrophosphatase should be added to the sample. (2) The metal ions selected do not or not substantially bind to DNA, NTP, dNTP and proteins. (3) The metal ions selected do not affect the chemical composition and structure of DNA and/or RNA. (4) The metal ions selected do not affect (e.g. inhibit) the polymerase used in the method. (5) The metal ions interact with the electrode used in such a way that slight changes in the concentration of metal ions can be measured.

By way of example, DNA is known to be damaged e.g. by platinum. Hence, such metals do not appear to be suitable.

In contrast, tin can be present in at least two oxidation stated, i.e. $Sn^{2+}$ and $Sn^{4+}$. It binds more specific to PPi (and Pi) than to ATP. It is assumed that tin does not bind strongly to DNA; it might, however, be necessary to additionally add magnesium to the sample. Thus, tin may be an alternative to manganese. Further, PPi (and/or Pi) binding metal ions are molybdenum Mo, gallium Ga, indium In, zirconium Zr and chromium Cr.

For identification of a suitable metal ion the candidate metal ion should be assessed with regard to the foregoing criteria if not known. For example, Cigala et al. describes the interaction of Sn' and $Zn^{2+}$ with phosphate ligands (Cigala et al. 2012. J. Molecul. Liquids. 165:143-153). Further, Sabbioni et al. describes the effect of different metal ions on HIV-1 reverse transcriptase (Sabbioni et al. 1999. Biol. Trace Element Res. 68:107-119).

Electrochemical Nucleic Acid Sequencing Apparatus

The invention further relates to an electrochemical nucleic acid sequencing apparatus comprising: (a) means for carrying out the steps of annealing and elongating a primer molecule to a template nucleic acid to be sequenced; and (b) an electrochemical cell comprising metal ions being capable of specifically binding to pyrophosphate and a working electrode responsive to said metalions. In a preferred embodiment the metal ions are manganese ions and the electrode is based on manganese oxide.

Figure 2:
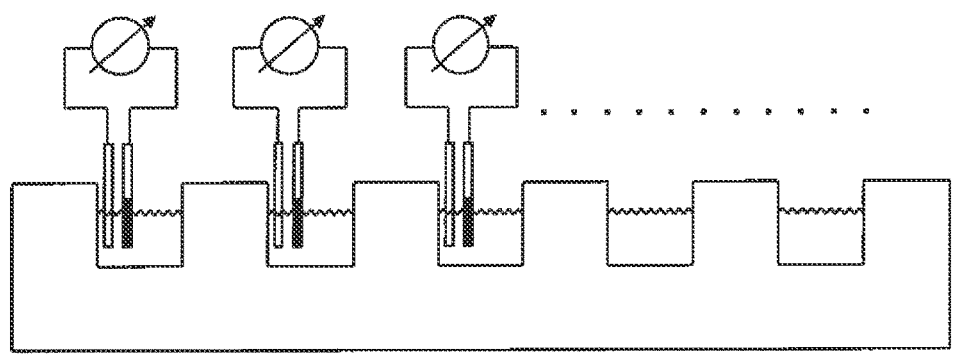
Figure 2:
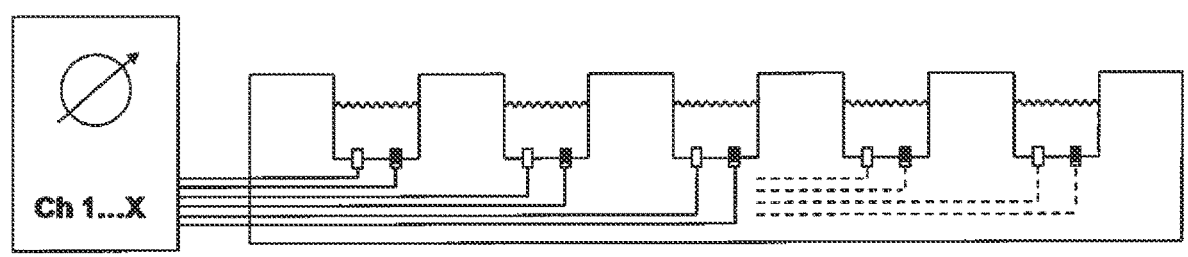

In a preferred arrangement these parts are combined in a small reaction chamber (see FIG. 2)

The means for carrying out the steps of annealing and elongating a primer may comprise a temperature control unit for heating and cooling, such as one or more peltier elements. It may also comprise means for supplying reagents and buffers to the reaction chamber. Such means can comprise one or more channels (e.g. tubes). Preferably the reagents and buffers can be supplied through different channels, i.e. one channel for each nucleotide or alternatively for all nucleotides, one channel for the sample, one channel for the polymerase, etc. The channels are preferably controllable, e.g. by valves.

FIGURE CAPTIONS

FIG. 1: $MnO_2$/Carbon-Paste-electrode measurement of different PCR cycles.

Manganese ions and their depletion by enzymatically generated pyrophosphate was followed by potentiometry using a manganese oxide/carbon paste electrode. For this purpose a template DNA was amplified by PCR using the following conditions:

Volume=500
dNTP10 mM 0.4
Forward Primer 10 mM 0.2 µl
Reverse Primer 10 mM 0.2 µl
Template 2 µl
Taq Polymerase 0.1 µl
10×Puffer (10 mM Tris, 50 mMKCI, 1.5 mM MgCl2) 2 ml
$MnCl_2$ 10 mM 0.4 µl Several samples from reaction mixtures after different numbers of PCR cycles yield different potentials (FIG. 1). It was shown that with a simple potential measurement the concentration of unbound $Mn^2$ ions can be analyzed in a complex mixture and thus the progress in the biochemical amplification reaction can be followed.

FIG. 2: Examples of the Electrochemical sequencing apparatus.

The upper part illustrates a measuring set up with a two electrode arrangement [metal ion sensitive working electrode (dark) and reference electrode (white)] dipping into the small reaction chambers and connected to a voltmeter. The lower part shows schematically an integrated version with enclosed working and reference electrodes within the reaction chambers.

The invention claimed is:

1. A method of detecting the formation or depletion of pyrophosphate in a sample comprising the steps of:
   a. providing a sample in which pyrophosphate is formed or depleted in a polymerase based amplification process;
   b. providing metal ions in said sample, wherein the metal ions are capable of specifically binding pyrophosphate in solution, wherein the metal ions are manganese ions;
   c. measuring in said sample the potential, current or charge at a first and a second electrode;
   d. comparing the potential, current or charge over time or between the first and second electrode with the formation or depletion of pyrophosphate in the sample, wherein at least one of the electrodes is selective for the manganese ions.

2. The method of claim 1, wherein the metal ions are unbound free manganese ions.

3. The method of claim 1, wherein the manganese ions do not bind to DNA, NTP, dNTP and proteins and the sample comprises DNA or dNTPs.

4. The method of claim 1, wherein the first or second electrode comprises manganese oxide.

5. A method of detecting the formation or depletion of pyrophosphate in a sample comprising the steps of:
   a. providing a sample in which pyrophosphate is formed or depleted in a polymerase based amplification process;
   b. providing metal ions in said sample, wherein the metal ions are capable of binding pyrophosphate in solution, wherein the metal ions are manganese ions;
   c. measuring in said sample the potential, current or charge at a first and a second electrode;
   d. comparing the potential, current or charge over time or between the first and second electrode with the formation or depletion of pyrophosphate in the sample, wherein the first or second electrode comprises manganese oxide.

* * * * *